US006929934B1

(12) United States Patent
Korchev et al.

(10) Patent No.: US 6,929,934 B1
(45) Date of Patent: Aug. 16, 2005

(54) OPTICAL MICROSCOPY AND ITS USE IN THE STUDY OF CELLS

(75) Inventors: Yuri Evgenievich Korchev, London (GB); David Klenerman, Cambridge (GB); Max Joseph Lab, London (GB)

(73) Assignee: Imperial College Innovations, Ltd., (GB)

( * ) Notice: Subject to any disclaimer, the term of this patent is extended or adjusted under 35 U.S.C. 154(b) by 0 days.

(21) Appl. No.: 10/030,868

(22) PCT Filed: Apr. 17, 2000

(86) PCT No.: PCT/GB00/01492

§ 371 (c)(1),
(2), (4) Date: Apr. 11, 2002

(87) PCT Pub. No.: WO00/63736

PCT Pub. Date: Oct. 26, 2000

(30) Foreign Application Priority Data

Apr. 19, 1999 (GB) .................................... 9908932
Oct. 20, 1999 (GB) .................................... 9924880

(51) Int. Cl.⁷ ........................ C12N 13/00; G01N 23/00
(52) U.S. Cl. .................................... 435/173.1; 250/306
(58) Field of Search ............................... 250/306, 243, 250/440.1; 435/173.1

(56) References Cited

U.S. PATENT DOCUMENTS

| 4,917,462 | A | * | 4/1990 | Lewis et al. ................. 359/368 |
| 4,924,091 | A | | 5/1990 | Hansma et al. |
| 5,105,305 | A | * | 4/1992 | Betzig et al. ................ 359/368 |
| 5,166,520 | A | | 11/1992 | Prater et al. |
| 5,254,854 | A | * | 10/1993 | Betzig ......................... 250/234 |
| 5,354,985 | A | * | 10/1994 | Quate .......................... 250/234 |
| 5,479,024 | A | | 12/1995 | Hillner et al. |
| 5,485,536 | A | * | 1/1996 | Islam ............................ 385/31 |
| 5,874,726 | A | | 2/1999 | Haydon |
| 6,621,079 | B1 | * | 9/2003 | Shao et al. ................... 250/306 |

FOREIGN PATENT DOCUMENTS

| JP | 09196936 | 7/1997 |
| JP | 09211010 | 8/1997 |
| WO | WO 98/37440 | 8/1998 |
| WO | WO 98/50791 A1 | 11/1998 |
| WO | WO 00/63736 | 10/2000 |

OTHER PUBLICATIONS

Lewis. A. et al. "Fountain Pen Nanochemistry: Atomic Force Control of Chrome Etching"*Applied Physics Letters*, Oct. 25, 1999. pp. 2689-2691, vol. 75, No. 17.

Korchev. Y, et al "Hybrid Scanning Ion Conductance and Scanning Near-Field Optical Microscopy for the Study of Living Cells"*Biophysical Journal*, May 2000, pp. 1-5, vol. 78.

Keller, T H "Scanning Near-Field Optical Microscopy in Reflection Mode Imaging in Liquid"*Rev. Sci. Intrum.*, Mar. 1997, pp. 1448-1454, vol. 68. No. 3.

Korchev, Y E "Scanning Ion Conductance Microscopy of Living Cells"*Biophysical Journal*. Aug. 1997, pp. 653-658, Vol. 73.

Hansma. P.K. "The Scanning Ion-Conductance Microscope"*Reports*. Feb. 3, 1989, pp. 641-643, vol. 243.

Jandt, K.D. "Development and Perspectives of Scanning Probe Microscopy (SPM) on Organic Materials Systems"*Materials Science and Engineering*, 1998, pp. 221-295, vol. 21.

Tan, W. "Optical Measurements on the Nanometer Scale"*Trends in Analytical Chemistry*, 1998, pp. 501-513, vol. 17, Nos. 8 and 9.

Korchev, Y. E. et al. "Specialized Scanning Ion-Conductance Microscope for Imaging of Living Cells"*Journal of Microscopy*, 1997, pp. 17-23, vol. 188, Part 1.

* cited by examiner

*Primary Examiner*—Jean C. Witz
*Assistant Examiner*—Susan Hanley
(74) *Attorney, Agent, or Firm*—Saliwanchik, Lloyd & Saliwanchik

(57) ABSTRACT

The present invention pertains to an apparatus for imaging an object, comprising a probe via which an assay component may be delivered; a sensor to detect ion current; and means for controlling the position of the probe relative to the object in response to the ion current. Such apparatus can be used to image live cells, without affecting them, in solution, e.g., using light, wherein the distance between probe and cell is less than the wavelength of light.

33 Claims, 4 Drawing Sheets

3pA | 400nm  200ms

3pA | 200ms 300 nm | 2μm

3pA | 2μm

OPTICAL MICROSCOPY AND ITS USE IN THE STUDY OF CELLS

This application is the U.S. national stage application of International patent application No. PCT/GB00/01492, filed May 17, 2000.

FIELD OF THE INVENTION

This invention relates to optical microscopy and its use in the study of cells.

BACKGROUND OF THE INVENTION

The cell is the most fundamental unit of living organisms, whether animal or plant. The study of its structure and composition, and how its various constituents function, lends valuable insight into the complex processes that occur in integrated biological systems. This requires techniques that allow investigation of cell samples to be conducted in real-time, non-invasively, and in solutions that mimic physiological conditions so that cell functionality is retained.

Optical microscopy (using visible light) has been widely applied to study live cells. However, the resolution is limited by diffraction to about 200–250 nm. For more detailed study, one commonly used method is electron microscopy, where it is possible to obtain images with 10 nm resolution, but the sample needs to be fixed prior to imaging. Hence, it is not possible to use an electron microscope to study living cells.

Another possible high resolution technique is based on the use of scanning probe microscopy (SPM), in which a sharp probe tip is scanned in close proximity to the sample understudy. The consequent interactions and thus the chemical/physical properties of the sample can be plotted as a function of the tip's position with respect to the sample, to generate a profile of this measured interaction. Members of the SPM family that are commonly applied to biological imaging are atomic free microscopy (AFM), scanning ion-conductance microscopy (SICM) and scanning near-field optical microscopy (SNOM).

In SNOM, light is normally coupled down a fibre-optic probe with an output aperture of sub-wavelength dimensions, which is scanned above the sample surface. Interaction forces between the tip and sample are used to maintain their separation at less than the sub-wavelength dimensions of the aperture. This arrangement allows simultaneous generation of optical and topographic images whose resolution depends on the size of the output aperture and the size of the tip respectively. As in far field optical microscopy, all contrast mechanisms are available in SNOM, and in particular chemical imaging is possible by the use of fluorescent labels. However, while it is straightforward to fabricate probes with smaller apertures, achieving smaller tip-sample separations in liquid (<60 nm) is difficult because of the problems in obtaining a reliable method of controlling the probe-sample distance. This is due to damping of the oscillations of the probe used in the feedback mechanism.

In SICM, an electrolyte-filled, glass micropipette is scanned over the surface of a sample bathed in an electrolytic solution; see Hansma et al (1989) Science 243:641–3. The pipette-sample separation is maintained at a constant value by controlling the ion-current that flows via the pipette aperture. The flow is between two electrodes: one inside the pipette and another outside in the electrolyte solution. For an applied bias between the electrodes, the ion-current signal depends on a combination of the micropipette's resistance ($R_P$) and the access resistance ($R_{AC}$) which is the resistance along the convergent paths from the bath to the micropipette opening. $R_P$ depends on the tip diameter and cone angle of the micropipette, whereas $R_{AC}$ displays complicated dependence on the sample's electrochemical properties, geometry and separation from the probe. It is $R_{AC}$ that lends ion-current sensitivity to the pipette-sample separation and allows its exploitation in maintaining the distance such that contact does not occur.

The optimum tip-sample separation that has allowed SICM to be established as a non-contact profiling method for elaborated surfaces, is equal to one-half of the tip diameter; see Korchev et al (1997), J. Microsc. 188:17–23, and also Biophys. J. 73:653–8. The tip's output is used to generate topographic features and/or images of the local ion-currents flowing through pores on the sample surface. The spatial resolution achievable using SICM is dependent on the size of the tip aperture, and is typically between 50 nm and 1.5 $\mu$m. This produces a corresponding resolution.

SUMMARY OF THE INVENTION

In order to meet the objective of high resolution microscopic study of cells that are alive, and not fixed, a hybrid scanning ion conductance and scanning near field optical microscope has been developed. Accordingly, in one aspect of this invention, apparatus comprises a probe via which an assay component may be delivered; a sensor to detect ion current; and means for controlling the position of the probe relative to the object in response to the ion current. In another aspect, a method for imaging an object in a liquid environment, by scanning ion-conductance microscopy, uses a probe whose distance from the object is maintained in response to the ion current in the liquid, wherein the probe includes means for delivering an assay component to the object.

The present invention is based in part on a realisation that SICM and SNOM techniques are complementary (SICM as a non-contact profiling method and SNOM as a technique that allows acquisition of optical and chemical information pertaining to a sample) and that they can be used to advantage if they are in one experimental arrangement.

Use of the novel apparatus allows quantitative, high-resolution characterisation of the cell surface and the simultaneous recording of topographic and optical images. A particular feature of the method is a reliable mechanism to control the distance between the probe and the sample in liquid, e.g. physiological buffer.

The new method has been demonstrated by recording near field images of living cells (cardiac myocytes) for the first time. Straightforward modifications to the instrument will enable fluorescence imaging and higher resolution.

The invention allows functional mapping of cells. For example, it allows ion channel mapping.

By means of the invention, it is possible to image the cell surface in a single scan, by using the probe to keep the cell surface in the confocal volume of the microscope. For biological imaging of live cells, the exposure of light can be limited, thereby minimising damage and overcoming the problem of intense near field light sources used in SNOM. Although the cell may alter shape, this is not a problem in this surface confocal mode, since imaging is always at the surface.

A feature of this invention is its simplicity. For example, existing confocal microscopes can readily be retrofitted with a pipette and suitable computer control.

DESCRIPTION OF THE DRAWINGS

A micropipette of the type that may be used in this invention is illustrated in FIG. 1 of the accompanying drawings. FIGS. 2B and 2C illustrate how feedback control may be used, as in a preferred embodiment of this invention.

DESCRIPTION OF THE INVENTION

The term "assay component" is used herein to describe any chemical or physical entity that can be delivered to the locus of observation, and which is either observable per se or can generate an observable response. For example, the assay component may be light; a laser may be provided, so that, for example, coherent light can be directed, via the probe, to a cell surface. Alternatively, possibly again in combination with a laser source, the probe may contain at its tip a material, such as a light-activatable dye, that will generate light in situ. The outer surface of the probe may be coated, e.g. with a metal layer, to prevent leakage of light.

Figure 1:
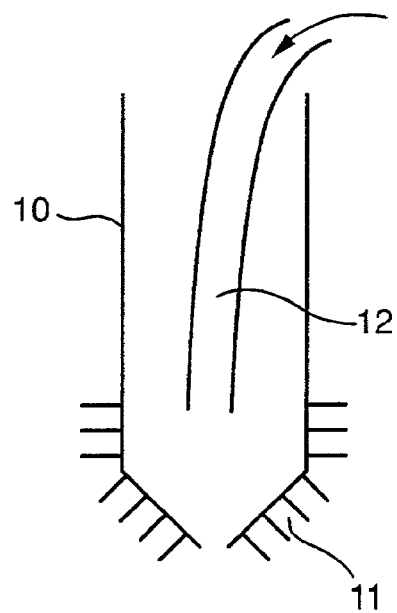

A suitable micropipette is shown schematically in FIG. 1. It comprises a pipette body 10 having the metal coating 11 at its tip. Laser light from a source (not shown) is launched down a fibre optic 12.

Thus, for example, a micropipette is filled with one or more fluorophors and excited with a laser. In one case, the laser comes up the microscope objective; this produces a local light source since the laser is focussed at the tip of the pipette. In addition, the dye is concentrated, so that the depth of penetration of the laser light into solution is very small. The dye is under pressure and so slowly leaks out of the pipette, avoiding problems in photobleaching. This can be used to image in the near field; no metal coating is required.

In another embodiment, the assay component is a chemical reagent, and this reagent may act directly or indirectly. Examples of reagents that have a direct effect include those that generate fluorescence, bioluminescence or chemiluminescence. Thus, for example, a micropipette may be adapted to deliver luciferin that is acted on by luciferase in the presence of ATP and magnesium ions, to produce light peaking at 568 nm. Magnesium may be provided in the solution and all the other reagents in the pipette, so that light is produced locally by the reaction. No coating is needed to produce the near field light source. Rapid dilution of reagents, once they emerge from the pipette, means that the light is produced at the tip and the resolution is determined by the aperture of the pipette.

Other suitable reagents include molecules that change fluorescence with variation in a particular property such as pH, in concentration, e.g. of Ca, or potential. Local application of appropriate reagents and excitation of the fluorophor allows local probing of this property, e.g. map channel or proton pumps.

Examples of reagents that act indirectly are those that, on delivery to the cell, product a change inside the cell, as a result of transduction. It is that change which is detected. This effect may be naturally amplified by the signal cascade.

More specifically, the pipette may contain a ligand or drug. This acts on or binds a receptor on the cell surface. Inside the cell, as a result of the signal transduction cascade, there is a change in the level of a secondary messenger, for example in the cell's calcium level. There is amplification of the binding event by the cascade where an enzyme is turned on, producing many product molecules which in turn act on many other enzymes etc., so that one binding event results in a large change. This naturally amplified signal is detected, for instance, using a fluorescence dye, e.g. fluor-3, which binds calcium in the cell, and can be used to measure calcium concentration. A large change in calcium can be seen when the pipette is over the receptor. Since calcium is the most common messenger used by the cell, this is a general method. It does not involve the use of fluorescently-labelled antibodies to detect where a receptor is located. Antibodies, particularly monoclonal, can be hard to produce and can have problems that they are internalised in the cell. Other fluorescence markers can be used for other common messengers in the cell, such as cAMP.

The present invention may be illustrated by modification of an existing SICM system, to allow simultaneous generation of SICM and SNOM images of living cardiac myocyte cells. In order to illustrate the utility of such apparatus, cardiac myocyte cells were chosen, for two main reasons. Firstly, they are composed of light and dark bands of material/striations that occur periodically, every 2.1 μm, which give them a distinct appearance and therefore make them a good model system for study. Secondly, and more importantly, they constitute heart muscle chambers that synchronously contract to produce the crucial pumping activity to circulate blood to the rest of the body. These cells have previously been studied using SICM (Korchev et al, supra).

The experiments presented here have provided the first images of live cells taken using scanning near field optical microscopy and show that scanning ion conductance microscopy provides a reliable control mechanism for SNOM imaging of live cells. The images of cardiomyocytes have the widely accepted structure and dimensions: comparable, for example, to those found with electron microscopy. By comparison, an important advantage of this invention is that the cells are unfixed and alive.

Although a simple hybrid SICM-SNOM instrument already has the potential to be a powerful investigative tool, straightforward modifications can be made, to improve its sensitivity and resolution. Firstly, smaller coated pipettes may improve both the SICM and SNOM resolution and increase the size of the optical signals, by holding the near field probe closer to the sample. For example, high resolution SNOM probes may be made by tapering and coating a micropipette for imaging in air using force control (Harootunian et al, 1986). An optical resolution less than 100 nm was obtained. This indicates that fabrication of higher resolution near field probes for SICM-SNOM is feasible. Using a higher numerical aperture objective for collection of the light can further increase the optical signal. These improvements will enable fluorescence imaging and also minimise problems in photobleaching and photodamage by working at minimum laser intensity. It is easier to photodamage living cells than fixed cells, so reducing the required laser power is important in order to be able to take multiple scans over time. These improvements in combination should enable the obtaining of simultaneous SICM and SNOM images with a resolution better than 100 nm on live cells.

In particular, by using the ion current to control the distance between a coated micropipette and the sample, it is possible to obtain simultaneous optical and SICM images. The optical images are obtained in the near field and hence this appears to be reliable way to perform SNOM imaging of live cells. This is the first time that has been achieved.

Straightforward improvements to the instrument should enable fluorescence imaging and higher resolution to be obtained. Combination with fluorescence imaging may allow one to image receptors and channels on the surface of live cells and to follow changes in the response to specific stimuli. The new method of SICM-SNOM imaging of live cells has a wide range of possible applications in biological science.

In a preferred embodiment of the invention, a frequency-modulated scanning protocol for a scanning ion conductance microscope (SICM) is used. This may comprise means to vibrate a SICM probe in a vertical direction (Z) and to use this modulation for feedback control of the microscope.

Figure 2A:
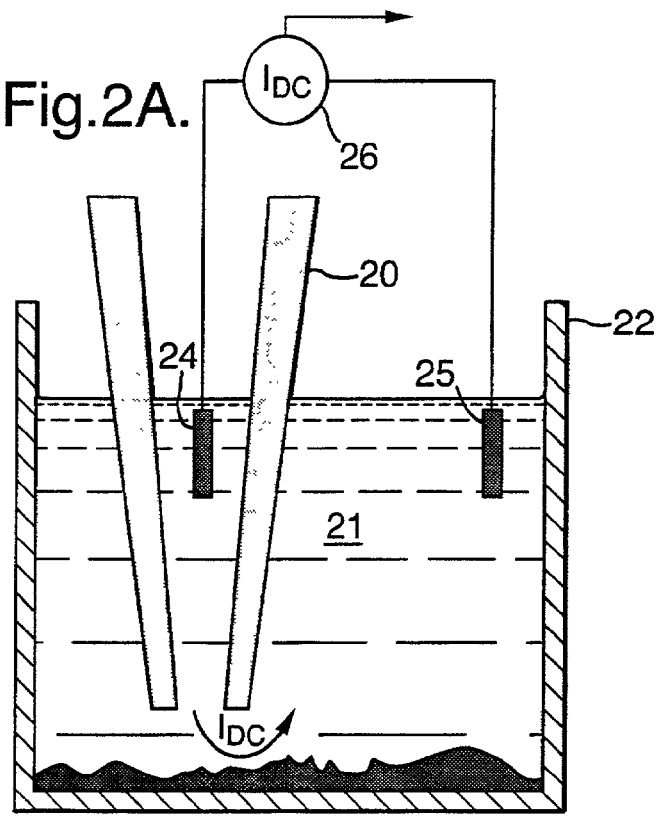
FIGS. 2A and 2C illustrate how non-modulated ion current may be used to control probe position over a sample.
Figure 2B:
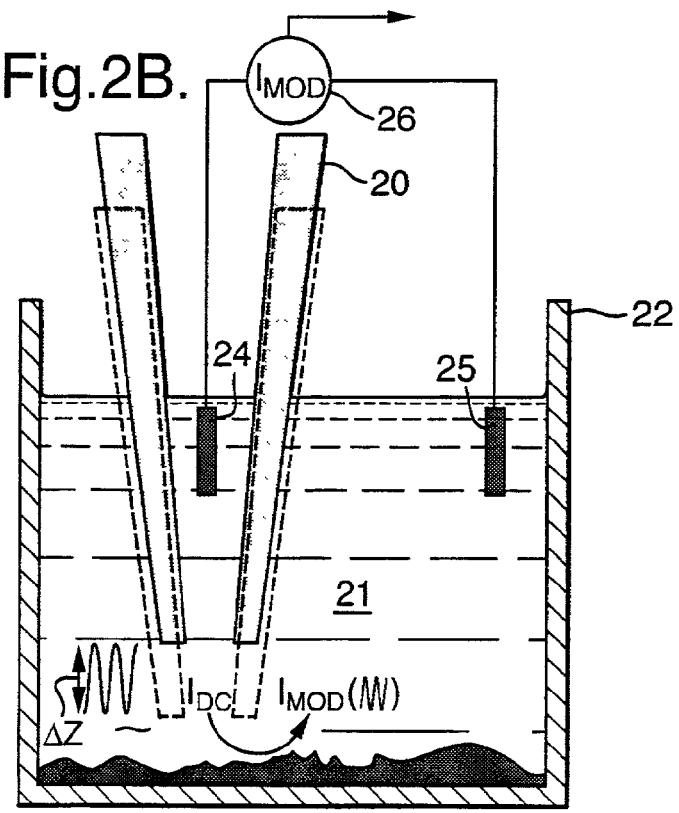
Figure 2C:
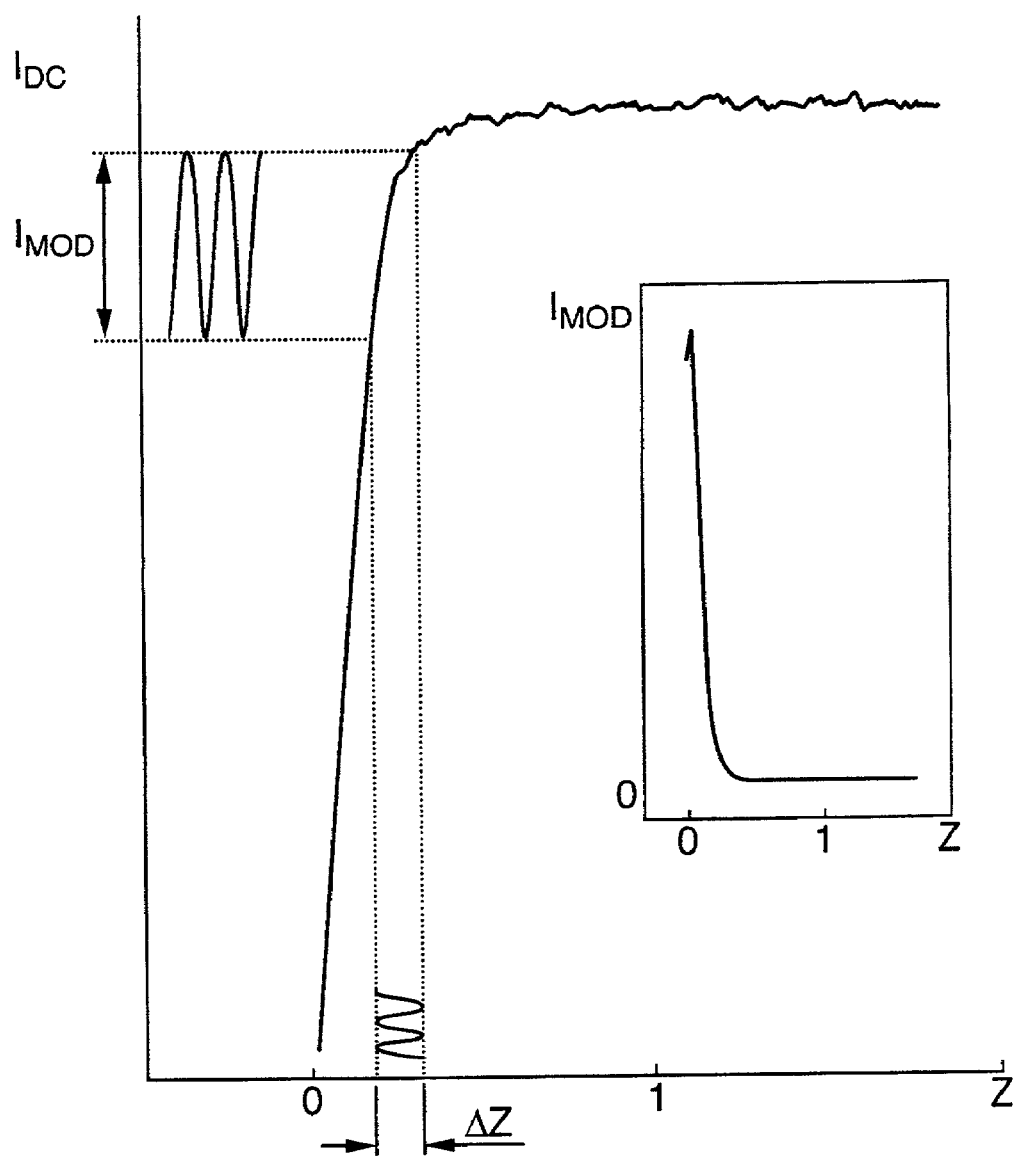

FIGS. 2A and 2B show schematically a micropipette 20 (also in dotted outline in FIG. 2B) in an electrolyte 21 within a vessel 22 having a sample 23 at its base. Electrodes 24 and 25 are connected via a circuit including a meter 26 providing feedback control (represented by the arrow). FIG. 2C shows tip current as a function of the sample-tip separation.

In conventional SICM microscopes, non-modulated ($I_{DC}$) ion current (FIGS. 2A and 2C) is used to control the probe position over the sample. In that case, any changes in ion current flowing through the micropipette tip which are not caused by the probe/sample interaction (changes in ion concentration, interaction of the micropipette tip with contaminating particles in aqueous solutions, drift of electrode potential, etc) produce artefacts or crash the sample and the micropipette. In the frequency-modulated mode of SICM operation, the movement of the microscope tip ($\Delta Z$) generates modulated current ($I_{MOD}$). This $I_{MOD}$ is only generated when the probe senses the sample and is used for feedback control of the microscope; see FIGS. 2B and 2C (insert). The feedback control mainly uses, for example, the frequency-modulated scanning protocol, as it has a number of additional advantages over a non-modulated mode: greater signal/noise ratio; high stability (ability to operate in a large gradient of electrolyte and with high $I_{DC}$ drift); higher scan speed; increase in lateral sensitivity.

A typical SICM system comprises components that feature in all SPMs, namely, scanning probe, piezo-actuator scanning elements, control electronics and a computer. These components may be built in and around an inverted microscope, e.g. Diaphot 200 (Nikon Corporation, Tokyo, Japan).

The following Examples illustrate the invention. Further evidence of the utility of this invention is provided, indirectly, by Lewis et al (1999), Applied Physics Letters 75(17): 2689–91. This utilises AFM, for control of chrome etching.

EXAMPLE 1

SICM probes are fabricated by pulling borosilicate glass microcapillaries with outer and inner diameters of 1.00 mm and 0.58 mm respectively, using a laser-based micropipette puller (Model P-2000, Sutter Instrument Co., San Rafael, Calif., USA). This reproducibly and easily produces probes with conical taper lengths and apex diameters of 200 nm, 400 nm and 1.0 $\mu$m, respectively.

Three-dimensional and high precision movement of the probe relative to the sample is achieved using a piezo-translation stage (Tritor 100, Piezosystem Jena, Germany) on which the SICM probe is mounted. The stage has a range of 100 $\mu$m in the x, y and z directions, so that scanning over biological samples, with features that scale up to 30–50 $\mu$m, is made possible. The high voltage required for deformation of the piezo-ceramic material that facilitates the stage's movement is provided by high voltage amplifiers (Piezosystem Jena, Germany). These amplifiers respond to appropriate signals generated by the control electronics, to drive the piezo-translation stage and achieve movement of the tip relative to the sample. In addition to being connected with the hardware aspect of the microscope, the control electronics interface with a computer that allows data acquisition and image analysis. The control/data acquisition hardware and software are produced by East Coast Scientific (Cambridge, UK).

The pipette-sample separation is maintained at a constant value by monitoring the ion-current that flows between Ag/AgCl electrodes in the micropipette and electrolyte solution in which the sample is immersed. Phosphate-buffered saline (PBS) solution is used for both filling the micropipette and the electrophysiological medium of the cardiac myocytes, so that concentration cell potentials and liquid junction potentials are not established. The ion-current is measured for DC voltages of 50 mV applied to the electrodes. It is amplified by means of a high-impedance operational amplifier (OPA 129, Bull Brown International, USA) and converted to a voltage signal over a resistance of $10^8$ $\Omega$. This signal is then inputted into the control electronics where it is used for feedback control and data acquisition.

The micropipette is housed in a special, custom-made holder which is assembled together with the current amplifier and piezo-translation stage to comprise the SICM head. The SICM head is mounted onto the arm of the inverted microscope's z-translator that facilitates coarse vertical positioning of the micropipette relative to the sample positioned immediately below it. The sample is contained in a petri dish which is placed on the microscope's stage. Movement of the sample relative to the micropipette is achieved by the x, y translation controls of the stage. The processes of monitoring the vertical position of the micropipette relative to the sample and selection of an area of interest on the sample can be viewed on a TV screen via a video camera (JVC TK-1280E, Victor Company, Japan).

Modifications were made, in order to permit simultaneous SICM and SNOM imaging. Laser light (Laser 2000 Ltd., UK) of wavelength 532 nm, was coupled via a multi-mode fibre (FG-200-UCR; 3M Specialty Optical Fibers, West Haven, USA) into the micropipette. In order to confine light of the aperture, 100–150 nm of aluminium was evaporated onto the walls of the pipette. The scattered laser light was collected by a x60 long working distance objective and relayed by transfer optics onto a PMT (D-104-814, Photon Technology International, Surbiton, England) to record the optical signal. During raster scan, this signal was recorded on the data acquisition computer, via an ADC, which also recorded the z position of the sample, to obtain simultaneous optical and topographic images of the sample using the control/data acquisition hardware and software.

Adult rabbit myocytes were isolated using a low calcium solution (NaCl 120, KCl 5.4, MgSO$_4$ 5, pyruvate 5, glucose 20, taurine 20, HEPES 10 and nitrotriacetic acid 5 (mmol/L), preoxygenated with 100% O$_2$) and collagenase and protease enzymes, as described by Jones et al (1990) Cardiovasc. Res. 24:834–842. Cells were imaged on a glass coverslip in a low calcium medium at room temperature.

Optical and SICM images were recorded simultaneously. It took about 20 minutes to record one set of images. The micropipette was estimated, by the measured ion current, to have an internal diameter of about 500 nm and was held about 250 nm over the surface during imaging. The estimated external diameter was 1000 nm, and comprises the glass and metal coating. This means that these images were recorded in the near field, less than the wavelength of light from the sample, with an aperture having a diameter comparable to the wavelength of light.

A 20×20 μm scan of the surface of a living rabbit cardiac myocyte showed that the sarcomeric structure was clearly visible in both the SICM and SNOM images. The optical image appeared to be generated only at the surface of the cell as expected using a scanning probe technique. In a larger scan range, there was excellent correspondence between the optical and SICM images. The estimated resolution was about 500 nm.

EXAMPLE 2

This Example again illustrates the focal, highly localized application of ions, agonists, or other agents to a membrane during a scan via the microscope micropipette. Monitoring the electrical response of the cell is conducted with a patch-clamp micropipette. This arrangement is illustrated schematically in FIG. 3.

Figure 3:
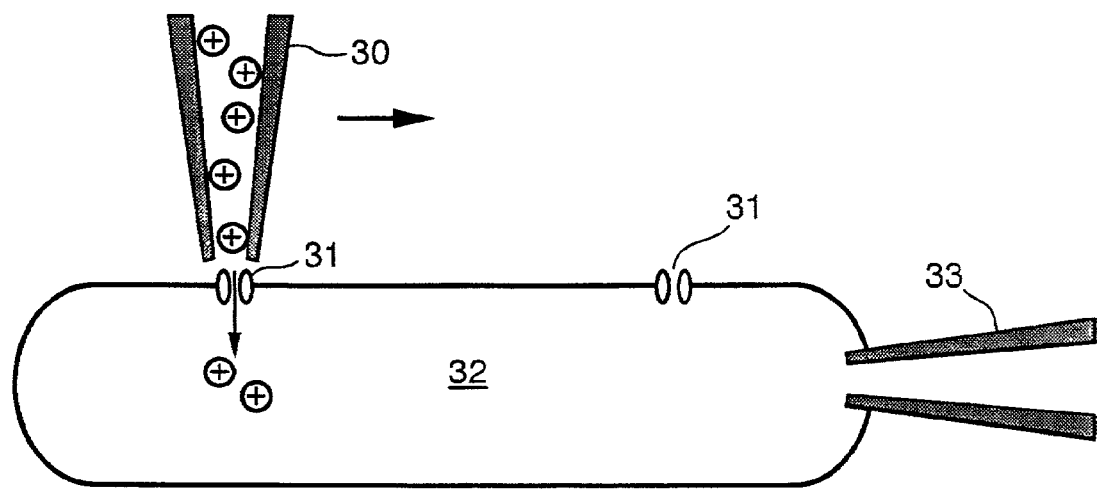
FIG. 3 represents another arrangement of components suitable for use in the invention.

More particularly, FIG. 3 shows schematically a scanning micropipette 30 whose tip is adjacent to an ion channel 31 in a cell 32. A patch clamp micropipette 33 provides ion channel current recording.

This Example investigates the distribution of ATP-regulated $K^+$ channels ($K_{ATP}$ channels) in rat cardiomyocyte sarcolemma. $K_{ATP}$ channels play important roles in the relaxation and preservation of cardiomyocytes during metabolic stress such as hypoxia or ischemia. Very little is known about their localization in the cell membrane. Experimental conditions were chosen so that intra- and extracellular solutions contain no $K^+$ ions, and the intracellular ATP concentration was reduced to provide maximum activation of $K_{ATP}$ channels.

Figure 4A:
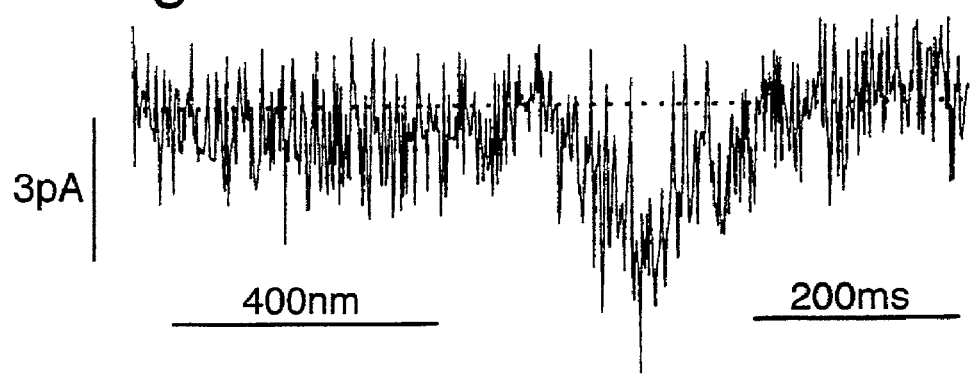
FIG. 4 shows the results of detection of single $K_{ATP}$ channels in rat cardiomyocyte sarcolemma.

Before measurements, the cell was perfused, and intracellular and extracellular $K^+$ was substituted by $Cs^+$ and $Na^+$ respectively. The intracellular solution contained no ATP. The cell was clamped at 0 mV. Prior to channel mapping, extracellular $Na^+$ was replaced for a short time by $K^+$ to ensure that the intracellular ATP level is sufficiently low to observe strong ATP-regulated $K^+$ current. Under these conditions, but in the presence of ATP, this current is not observed. The microscope micropipette probe contains permeable ions—$K^+$ (1 M), and as it scans the cell surface, it supplies $K^+$ ions to a highly localized area under the micropipette tip. When $K^+$ concentration increases near the active ion channel, the patch-clamp micropipette records increased $K^+$ current (FIG. 4A). The dotted line represents zero current.

Figure 4B:
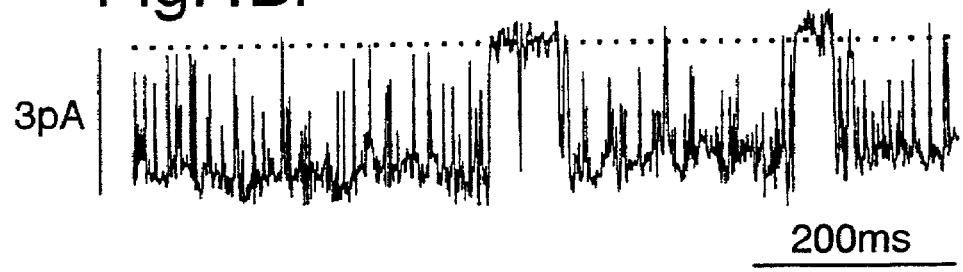

The observed ion current profile is bell-shaped, which is as expected from the distribution of $K^+$ ions around the micropipette tip. The maximum value of negative current corresponds to the position of the scanning micropipette tip when it is exactly above the ion channel, and is proportional to the $K^+$ concentration in the micropipette. This current value closely matches the amplitude of single $K_{ATP}$ channel current observed in outside-out patches studied under similar ionic conditions (FIG. 4B), where the bath $K^+$ concentration is equal to that supplied by the scanning micropipette.

Figure 4C:
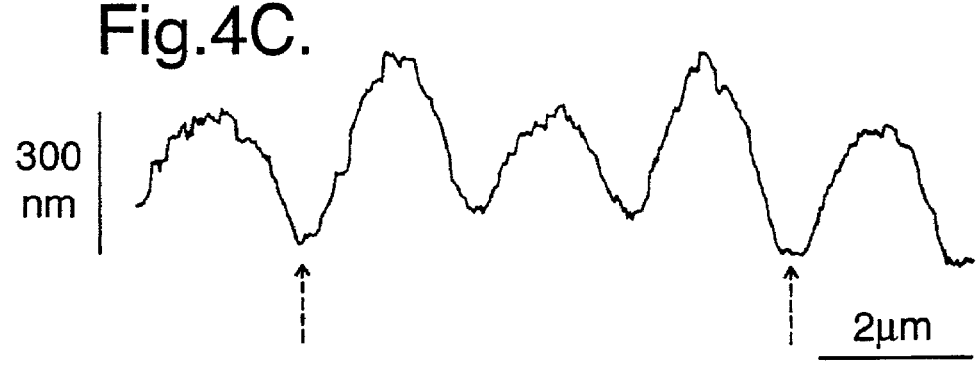
Figure 4D:

These procedures allow two images (shown as the single profiles across a cardiac myocyte surface, FIGS. 4C & 4D) to be obtained simultaneously. One is the topographical image of the cell surface (FIG. 4C). The other is an 'ion current' image (FIG. 4D), where each point corresponds to the value of ion current measured by the patch clamp pipette. This is plotted using the co-ordinates of the microscope micropipette tip on the cell surface at the time of measurement. Two current peaks directed downwardly, that correspond to the positions of individual ion channels, are clearly visible in FIG. 4D, and vertical arrows indicate their positions on the cardiac myocyte surface (FIG. 4C).

Active ion channels spend part of their time in the closed state and can easily remain undetected during a short period of measurement. In order to increase the probability of single channel detection, the current was acquired through the same single channel during several profile records of the scan.

Analysis of a large number of current images revealed that $K_{ATP}$ channels are non-uniformly distributed, being concentrated in the localized regions of the cardiac myocyte sarcolemma. Each of these regions or "clusters" is separated by 2–6 μM from the others and contains up to 10 active ion channels. The ion channels within the "cluster" are 0.2–1 μm apart. The $K_{ATP}$ channels could be recorded at the same locations in the sarcolemma during relatively long periods of observation (more than 40 min). Furthermore, the active $K_{ATP}$ channels were observed only in "scallop"-like regions of sarcolemma, and not in other parts of the plasma membrane (e.g. the regions of cellular contacts). This suggests that the $K_{ATP}$ channels are anchored, probably by the cytoskeleton, in specific regions of the sarcolemma and have very low lateral mobility. This direct observation is in good accord with published results, that indicate that there is some link between the F-actin cytoskeleton and the $K_{ATP}$ channels; see Yokoshiki et al, Pflugers Arch. 434–203 (1997).

This technique can be used to study the distribution of other types of ion channels in cardiomyocytes. Also, the approach will have general application in the investigation of the ion channel functional localization in intact cell membranes of different cell types.

What is claimed is:

1. An apparatus for imaging an object comprising a container in which an object can be immersed in a first electrolyte solution, a probe capable of containing a second electrolyte solution, wherein said electrolyte solutions can be in fluid communication, wherein said probe can deliver an assay component to said object; a means for vibrating said probe at a given frequency substantially normal to the surface of the object; a means to detect ion current flowing between said probe and said container comprising a first electrode disposed in said probe and a second electrode disposed in said container in which said object is immersed; means for monitoring modulation of the ion current resulting from the vibration of said probe at the given frequency while close to the surface of the object; and a means to control the distance of the probe from the surface of the object in response to the modulation of the ion current.

2. The apparatus according to claim 1, wherein said probe is a micropipette.

3. The apparatus according to claim 1, wherein said assay component is light.

4. The apparatus according to claim 2, wherein said assay component is light.

5. The apparatus according to claim 3, wherein said probe comprises a fiber optic.

6. The apparatus according to claim 3, which additionally comprises a laser light source.

7. The apparatus according to claim 5, which additionally comprises a laser light source.

8. The apparatus according to claim 3, wherein said probe contains a light-activatable dye at its tip.

9. The apparatus according to claim 3, wherein the outer surface of said probe is coated to prevent leakage of light.

10. The apparatus according to claim 3, wherein the outer surface of said probe is coated with a metal layer to prevent leakage of light.

11. The apparatus according to claim 1, wherein said assay component comprises a substance that produces a detectable change in response to interacting with the surface of a live cell.

12. The apparatus according to claim 2, wherein said assay component comprises a substance that produces a detectable change in response to interacting with the surface of a live cell.

13. The apparatus according to claim 11, wherein said substance generates fluorescence, bioluminescence or chemiluminescence.

14. The apparatus according to claim 12, wherein substance generates flourescence, bioluminescence or chemiluminescence.

15. The apparatus according to claim 1, wherein said assay component comprises a substance that produces a detectable change in response to interacting with the inside of a live cell.

16. The apparatus according to claim 2, wherein said assay component comprises a substance that produces a detectable change in response to interacting with the inside of a live cell.

17. A method for imaging an object in a container in a liquid environment, by scanning ion conductance microscopy, which comprises immersing said object in a first electrolyte liquid, placing a probe in said container with said object, wherein said probe contains a second electrolyte liquid, placing a first electrode in said probe and a second electrode in said container having said immersed object, vibrating said probe close to the object, at a given frequency, substantially normal to the surface of the object, wherein said vibration causes an ion current between said first electrode disposed within said probe and said second electrode in said container having said immersed object, detecting the ion current, monitoring modulation of the ion current resulting from said vibration of said probe while close to the surface of the object, controlling the distance of said probe from the surface of the object in response to the modulation of the ion current, wherein said probe includes a means for delivering an assay component to the object.

18. The method according to claim 17, wherein said probe is a micropipette.

19. The method according to claim 17, wherein said probe comprises a fiber optic.

20. The method according to claim 17, wherein said probe contains a light-activatable dye at its tip.

21. The apparatus according to claim 17, wherein the outer surface of said probe is coated with a metal layer to prevent leakage of light.

22. The method according to claim 17, wherein said assay component comprises a substance that produces a detectable change in response to interacting with the surface of a live cell.

23. The method according to claim 18, wherein said assay component comprises a substance that produces a detectable change in response to interacting with the surface of a live cell.

24. The method according to claim 23, wherein said substance generates fluorescence, bioluminescence or chemiluminescence.

25. The apparatus according to claim 17, wherein said assay component comprises a substance that produces a detectable change in response to interacting with the inside of a live cell.

26. The apparatus according to claim 18, wherein said assay component comprises a substance that produces a detectable change in response to interacting with the inside of a live cell.

27. The method according to claim 17, wherein the assay component is light.

28. The method according to claim 27, which additionally comprises a laser light source.

29. The method according to claim 26, wherein said substance generates fluorescence, bioluminescence or chemiluminescence.

30. The method according to claim 17, which comprises generating light and wherein the said distance is less than the wavelength of the light.

31. The method according to claim 17, wherein the object is a live cell.

32. An apparatus for imaging an object, comprising a container in which an object can be immersed in a first electrolyte solution, a probe capable of containing a second electrolyte solution, wherein said electrolyte solutions can be in fluid communication, wherein said probe contains an assay component that can be delivered to the locus of said object; wherein said assay component is a substance that can interact chemically or physically with said object; a means for vibrating said probe at a given frequency substantially normal to the surface of the object; a means to detect ion current flowing between said probe and said container comprising a first electrode disposed in said probe and a second electrode disposed in said container in which said object is immersed; means for monitoring modulation of the ion current resulting from the vibration of said probe at the given frequency while dose to the surface of the object; and a means to control the distance of said probe from the surface of the object in response to the modulation of the ion current.

33. The apparatus according to claim 32, wherein said probe is a micropipette.

\* \* \* \* \*

UNITED STATES PATENT AND TRADEMARK OFFICE
CERTIFICATE OF CORRECTION

PATENT NO. : 6,929,934 B1
DATED : August 16, 2005
INVENTOR(S) : Yuri Evgenievich Korchev, David Klenerman and Max Joseph Lab It is certified that error appears in the above-identified patent and that said Letters Patent is hereby corrected as shown below:

Column 10,
Line 48, "while dose to" should read -- while close to --.

Signed and Sealed this

Fourth Day of October , 2005

JON W. DUDAS
*Director of the United States Patent and Trademark Office*